United States Patent [19]

Molzahn et al.

[11] Patent Number: 4,927,931
[45] Date of Patent: May 22, 1990

[54] PREPARATION OF ALKYL-EXTENDED, ALCOHOL-EXTENDED OR AMINE-EXTENDED PIPERAZINES

[75] Inventors: David C. Molzahn; George E. Hartwell; Robert G. Bowman, all of Midland, Mich.

[73] Assignee: The Dow Chemical Company, Midland, Mich.

[21] Appl. No.: 265,610

[22] Filed: Nov. 1, 1988

[51] Int. Cl.$^5$ .................... D01J 23/20; C07D 241/02
[52] U.S. Cl. ..................................... 544/357; 502/353
[58] Field of Search ............. 540/358, 404, 402; 544/337; 502/353

[56] References Cited

U.S. PATENT DOCUMENTS

| | | | |
|---|---|---|---|
| 3,037,025 | 11/1962 | Godfrey | 260/268 |
| 3,068,232 | 11/1962 | Moss | 260/268 |
| 3,231,616 | 1/1966 | Jones | 260/581 |
| 3,364,218 | 9/1968 | Brader | 260/268 |
| 3,956,329 | 5/1976 | Murakami et al. | 260/268 SY |
| 4,036,881 | 7/1977 | Brennan et al. | 549/357 |
| 4,049,657 | 9/1977 | Brennan et al. | 544/357 |
| 4,217,240 | 8/1980 | Bergna | 252/313 S |
| 4,376,732 | 3/1983 | Ramirez | 544/357 |
| 4,400,306 | 8/1983 | Dria et al. | 544/357 |
| 4,495,369 | 1/1985 | Werner et al. | 564/480 |
| 4,552,961 | 10/1985 | Herdle | 544/402 |
| 4,582,904 | 4/1986 | Wells et al. | 544/178 |
| 4,613,705 | 9/1986 | Hargis | 564/409 |
| 4,622,310 | 11/1986 | Iacobucci | 502/208 |
| 4,652,544 | 3/1987 | Okazaki et al. | 502/208 |
| 4,698,427 | 10/1987 | Vanderpool | 544/404 |

FOREIGN PATENT DOCUMENTS

| | | |
|---|---|---|
| 0256516 | 2/1988 | European Pat. Off. |
| 4896475 | 12/1973 | Japan . |
| 58-35179 | 3/1983 | Japan . |
| 2147896 | 2/1985 | United Kingdom . |

OTHER PUBLICATIONS

Chemical Abstracts 87:201551a (1977).
Derwent 55652C/32 (1980).
Chemical Abstracts 87:23209k (1977).

*Primary Examiner*—Mukund J. Shah
*Assistant Examiner*—E. C. Ward

[57] ABSTRACT

A process for preparing alkyl-extended, alcohol-extended or amine-extended piperazines or mixtures thereof comprising contacting a difunctional aliphatic alcohol with a reactant amine, wherein at least one of the aliphatic alcohol or the reactant amine contains a piperazine moiety, in the presence of a catalyst containing a Group VB metal oxide or a Group VB metal phosphate, or mixtures thereof. For example, monoethanolamine reacts with piperazine in the presence of a catalyst of niobic acid supported on hydrated alumina to yield predominantly N-(2-aminoethyl)piperazine. Also, N-hydroxyethylpiperazine reacts with piperazine in the presence of a catalyst of niobium phosphate to yield predominantly 1,2-bis(piperazinyl)ethane.

29 Claims, No Drawings

PREPARATION OF ALKYL-EXTENDED, ALCOHOL-EXTENDED OR AMINE-EXTENDED PIPERAZINES

BACKGROUND OF THE INVENTION

This invention relates to a process for preparing alkyl-extended piperazines, such as 1,4-diethylpiperazine, and alcohol-extended piperazines, such as N-(2-hydroxyethyl)piperazine. This invention also relates to a process for preparing amine-extended piperazines, such as N-(2-aminoethyl)piperazine, bis(piperazinyl)alkanes, and oligo(piperazinylalkanes).

Alkyl-extended, alcohol-extended, and amine-extended piperazines are useful intermediates in the preparation of melt adhesive polymers and fine industrial chemicals, including veterinary antihelmintic pharmaceuticals, insecticides, and high temperature lubricating oils.

U.S. Pat. No. 3,364,218 teaches the self-condensation of N-(2-hydroxyethyl)piperazine to poly-1,4-ethylenepiperazine in the presence of hydrogen and a solid acid catalyst, such as silica-alumina, alumina, tungsten oxide, aluminum phosphate, and acid clays. It is difficult to control the degree of polymerization in this process. Accordingly, it is difficult to obtain high yields of N-(2-aminoethyl)piperazine, 1,2-bis(piperazinyl)ethane, tris(piperazinylethane), or other lower oligo(piperazinylethanes). Moreover, cyclic compounds, such as 1,4-diaza-[2.2.2]-bicyclooctane, are produced as undesirable by-products. In addition, the catalysts employed in this process lose their physical integrity in the presence of amines and water; therefore, the process is hampered by catalyst losses and separation problems.

U.S. Pat. No. 4,552,961 discloses a process for the preparation of polyalkylene polypiperazines comprising reacting piperazine with alkylene glycols or alkanolamines in the presence of a catalyst of phosphorus amide. Disadvantageously, this catalyst is homogeneous and must be separated from the product stream.

It would be advantageous to have a catalytic process for preparing alkyl-extended, alcohol-extended, or amine-extended piperazines. It would be more advantageous if the degree of polymerization of such a process could be controlled, and selective alkyl-extended, alcohol-extended or amine-extended piperazines could be prepared in high yields. It would be even more advantageous, if the catalyst for such a process was insoluble in the reaction mixture. With an insoluble catalyst the problems of leaching, plugging, and catalyst separation would be avoided, and the amination process would be more suitable for industrial adaptation.

SUMMARY OF THE INVENTION

In one aspect this invention is a process for preparing alkyl-extended, alcohol-extended, or amine-extended piperazines, or mixtures thereof comprising contacting in the presence of a catalyst an aliphatic alcohol with a reactant amine, wherein at least one of the aliphatic alcohol or reactant amine contains a piperazine moiety. The catalyst is a composition containing a Group VB metal. Preferably, the catalyst is a composition containing a Group VB metal oxide, a Group VB metal phosphate, or mixtures thereof. The contacting is conducted under reaction conditions such that a mixture of alkyl-extended, alcohol-extended or amine-extended piperazines is produced.

Advantageously, the process of this invention is capable of producing a wide range of alkyl-extended, alcohol-extended, or amine-extended piperazines in high selectivity. Moreover, the process of this invention does not produce significant amounts of undesirable cyclic by-products. More advantageously, the catalyst of this invention is insoluble in the reaction mixture: therefore, catalyst losses are minimized and separation of the product stream from the catalyst is relatively easy. These combined advantages render the process of this invention suitable for industrial use.

Alkyl-extended, alcohol-extended and amine-extended piperazines are useful intermediates in the preparation of melt adhesive polymers and fine industrial chemicals, including veterinary antihelmintic pharmaceuticals, insecticides, and high temperature lubricating oils.

In another aspect this invention is a process of preparing a catalyst composition containing a Group VB metal phosphate supported on a refractory oxide comprising (a) supporting a Group VB metal chloride on a refractory oxide, and (b) heating the supported Group VB metal chloride in the presence of phosphoric acid under conditions such that a catalyst containing a Group VB metal phosphate supported on a refractory oxide is formed.

DETAILED DESCRIPTION OF THE INVENTION

The products of the process of this invention are alkyl-extended, alcohol-extended, or amine-extended piperazines, or mixtures thereof. These products are described in detail hereinafter; but, are easily illustrated by the following four examples. The first comprises N-ethylpiperazine or N,N'-diethylpiperazine, which are alkyl-extended piperazines and which are prepared by reacting ethanol with piperazine. The second comprises N-(2-hydroxyethyl)piperazine, which is an alcohol-extended piperazine and which is prepared by reacting ethylene glycol with piperazine. The third comprises N-(2-aminoethyl)piperazine, which is an amine-extended piperazine and which is prepared by reacting monoethanolamine with piperazine. The fourth comprises 1,2-bis(piperazinyl)ethane, which is also an amine-extended piperazine and which is prepared by reacting N-(2-hydroxyethyl)piperazine with piperazine. It is observed that in each example the products are linearly-extended materials obtained by the condensation of an aliphatic alcohol with a reactant amine.

At least one of the reactants must contain a piperazine moiety in order for the process to yield an alkyl-extended, alcohol-extended, or amine-extended piperazine product. Accordingly, it is within the scope of this invention for the aliphatic alcohol to contain the piperazine moiety, as in the amination of N-(2-hydroxyethyl)piperazine by ammonia, a primary or secondary aliphatic amine. Likewise, it is within the scope of this invention for the reactant amine to contain the piperazine moiety, as in the amination of ethylene glycol by piperazine or N-(2-aminoethyl)piperazine. It is also within the scope of the invention for both the difunctional alcohol and the reactant amine to contain a piperazine moiety, as in the amination of N-(2-hydroxyethyl)piperazine by piperazine to yield 1,2-bis(piperazinyl)ethane. It is to be understood, therefore, that at least one of the aliphatic alcohol or the reactant amine must contain a piperazine group. Preferably, the reactant amine contains the piperazine moiety and this piperazine moiety participates in the amination reaction. Preferably, therefore, the reactant amine has an exposed or terminal piperazine moiety. Such preferred reactant amines include piperazine, itself, and N-aminoethylpiperazine.

The aliphatic alcohols which are employed in the process of this invention include any aliphatic alcohol containing at least one hydroxyl moiety bound to a primary carbon atom. Such alcohols include simple monofunctional primary alcohols, such as methanol, ethanol, n-propanol, n-butanol, n-pentanol, n-hexanol, n-heptanol, n-octanol, n-nonanol, n-decanol, as well as higher homologues. Additionally, difunctional aliphatic alcohols can be employed in the process of this invention provided that they contain (a) at least one hydroxyl moiety bound to a primary carbon atom, and (b) at least one additional moiety selected from the group consisting of hydroxyl, primary amine or secondary amine functionalities. Examples of suitable difunctional alcohols include diols such as ethylene glycol and propylene glycol, triols such as glycerol, and higher polyols; polyether polyols such as diethylene glycol, ethylene oxide capped polypropylene glycols, and higher homologues; alkanolamines such as monoethanolamine and N-(2-aminoethyl)ethanolamine; polyether amino alcohols such as 2-($\beta$-aminoethoxy)ethanol; and hydroxyalkyl-substituted piperazines, such as N-(2-hydroxyethyl)piperazine, N,N'-bis(2-hydroxyethyl)piperazine, and N-(2-hydroxyethyl)bispiperazines. The aliphatic alcohols are not limited to the aforementioned examples, and other equally suitable aliphatic alcohols can be employed in the practice of this invention.

In those reactions wherein the aliphatic alcohol does not contain a piperazine moiety, the preferred alcohols are represented by the general formula:

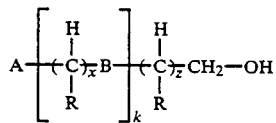

wherein A is H, OH or NHR; each B is independently NR or O; each R is independently hydrogen, hydroxy, amino ($NH_2$), an alkyl moiety of $C_1$-$C_{12}$ carbon atoms such as methyl, ethyl or propyl, a hydroxyalkyl or aminoalkyl moiety of $C_1$-$C_{12}$ carbon atoms, or a monocyclic aromatic moiety, such as phenyl, or tolyl; x is an integer from 2 to about 12; k is an integer from 0 to about 150; and z is an integer from 0 to about 12. Some examples of difunctional alcohols which satisfy this formula include monoethanolamine, ethylene glycol, propylene glycol, and N-(2-aminoethyl)ethanolamine. Preferably, each R is hydrogen. More preferably, each R is hydrogen, x is 2, and z is 1. Most preferably, each R is hydrogen, A is $NH_2$, k is 0, z is 1, and the difunctional alcohol is monoethanolamine.

In those reactions wherein the difunctional aliphatic alcohol contains a piperazine moiety, the preferred difunctional alcohols are represented by the general formula:

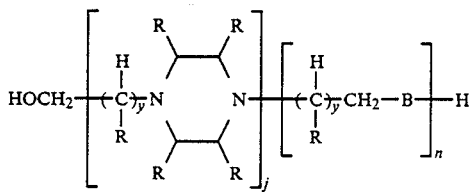

wherein each B is independently NR or O; each R is independently hydrogen, hydroxy, amino ($NH_2$), an alkyl moiety of $C_1$-$C_{12}$ carbon atoms such as methyl, ethyl or propyl, a hydroxyalkyl or aminoalkyl moiety of $C_1$-$C_{12}$ carbon atoms, or a monocyclic aromatic moiety, such as phenyl, or tolyl; each y is independently an integer from 0 to about 12; j is an integer from 1 to about 6; and n is an integer from 0 to about 6. Some examples of difunctional alcohols which satisfy this formula are N-(2-hydroxyethyl)piperazine, N-(2-hydroxyethyl)bispiperazine, N,N'-bis(2-hydroxyethyl)piperazine, and N,N'-bis(2-hydroxyethyl)bispiperazine. Preferably, each R is hydrogen. More preferably, each R is hydrogen, each y is independently 1 or 2, j is 1 or 2, n is 0-2, and each B is NR. Most preferably, each R is hydrogen, y is 1, j is 1, n is 0, and the compound is N-(2-hydroxyethyl)piperazine.

The reactant amines which are employed in the process of this invention include ammonia and any primary or secondary aliphatic amine which is capable of aminating the aliphatic alcohol. Examples of suitable reactant amines include primary and secondary monoamines such as ethylamine, propylamine, n-butylamine, hexylamine, octylamine, diethylamine, dipropylamine, dibutylamine, dihexylamine, dicyclohexylamine, and dioctylamine; linear and branched alkylene diamines or polyamines such as ethylenediamine, propylenediamine, diethylenetriamine, triethylenetetramines, and tetraethylenepentamines; alkylated linear polyamines such as N-(ethyl)ethylenediamine: alkylene ether polyamines such as 2-($\beta$-aminoethoxy)ethylamine: piperazine and oligo(piperazinyl alkanes) such as bispiperazines and trispiperazines; aminoalkyl-substituted piperazines such as N-(2-aminoethyl)piperazine and N,N'-bis(2-aminoethyl)piperazine; and mixtures of the above-identified amines. While the aforementioned reactant amines are representative of those which are suitable in the process of this invention, other reactant amines not recited herein may be equivalent and equally suitable.

In those reactions wherein the reactant amine does not contain a piperazine moiety and is an alkylenepolyamine or alkylene ether polyamine, the preferred species are represented by the general formula:

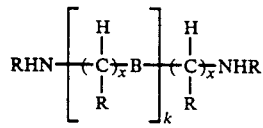

wherein each B is independently NR or O; each R is independently hydrogen, hydroxy, amino, an alkyl moiety of $C_1$-$C_{12}$ carbon atoms such as methyl, ethyl or propyl, a hydroxyalkyl or aminoalkyl moiety of $C_1$-$C_{12}$ carbon atoms, or a monocyclic aromatic moiety, such as phenyl, or tolyl; each x is independently an integer from 2 to about 12, and k is an integer from 0 to about 150.

Some examples of reactant amines which satisfy this formula include ethylenediamine, diethylenetriamine, 2,2'-di(aminoethyl)ether, and triethylenetetramine. Preferably, each B is NR and the amine is an alkylenepolyamine. More preferably, each B is NR and each R is hydrogen Most preferably, each B is NR, each R is hydrogen; each x is 2, and the amine is an ethylenepolyamine.

In those reactions wherein the reactant amine contains a piperazine moiety, preferred piperazines or aminoalkyl-substituted piperazines are represented by the general formula:

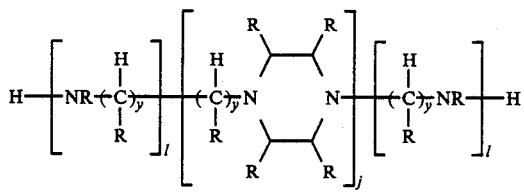

wherein each R is independently hydrogen, hydroxy, amino, an alkyl moiety of $C_1$–$C_{12}$ carbon atoms such as methyl, ethyl or propyl, a hydroxyalkyl or aminoalkyl moiety of $C_1$–$C_{12}$ carbon atoms, or a monocyclic aromatic moiety, such as phenyl, or tolyl; each y is independently an integer from 0 to about 12; each l is independently an integer from 0 to about 6; and j is an integer from 1 to about 6. Some examples of reactant amines which satisfy this formula include piperazine, N-(ethyl)-piperazine, N-(2-aminoethyl)piperazine, N,N'-bis(2-aminoethyl)piperazine, 1,2-bis(piperazinyl)ethane, and N-(2-aminoethyl)bispiperazine. Preferably, each R is hydrogen. More preferably, each R is hydrogen, y is 1 or 2, j is 1 or 2, and l is 0–2. Most preferably, each R is hydrogen, y is 0, j is 1, and each l is 0, and the compound is piperazine.

In accordance with the process of this invention, any mole ratio of reactant amine to aliphatic alcohol which enables the amination reaction to proceed to the desired alkyl-extended, alcohol-extended or amine-extended piperazine products is suitable. Typically, the aliphatic alcohol is reacted with at least about one mole equivalent of reactant amine; however, an excess of reactant amine can be advantageously employed. Preferably, the mole ratio of reactant amine to aliphatic alcohol is in the range from about 0.1 to about 20. More preferably, the mole ratio of reactant amine to aliphatic alcohol is in the range from about 0.5 to about 15; most preferably from about 1 to about 10.

Although, preferably, a solvent is not used in the amination reaction, it is within the scope of the invention for a solvent to be used, if desired. Any solvent is acceptable provided that (1) it is not reactive with the aliphatic alcohol, the reactant amine, or product piperazines, and (2) it does not decompose under the conditions of the reaction. Some examples of suitable solvents include water, saturated aliphatic hydrocarbons such as pentane, hexane, heptane, octane, nonane, and decane, and aromatic hydrocarbons such as benzene, toluene, and xylene. The amount of solvent employed depends on the particular reactants and reaction conditions. Any amount of solvent is acceptable that meets the intended purpose of use. Typically, the solvent constitutes from about 5 weight percent to about 95 weight percent of the feed stream. Preferably, the solvent constitutes from about 10 weight percent to about 80 weight percent of the feed stream.

The catalyst employed in the process of this invention is a composition containing a Group VB metal. Preferably, the composition contains a Group VB metal phosphate compound, a Group VB metal oxide compound, or mixtures thereof. The Group VB metals include vanadium, niobium, and tantalum. Examples of suitable Group VB metal phosphate compounds include vanadium phosphates such as $V_2O_5.P_2O_5$ niobium phosphates such as $2Nb_2O_5.P_2O_5.6H_2O$, $2Nb_2O_5.P_2O_5$, $NbOPO_4$, $PNb_9O_{25}$; and tantalum phosphates such as $2Ta_2O_5.P_2O_5.6H_2O$, $2Ta_2O_5.P_2O_5$, $TaOPO_4$. Group VB metal meta-phosphates, fluorophosphates, hydrated phosphates, silico-phosphates and non-stoichiometric phosphate compounds are also suitable, as are Group VB metal hydrogen phosphates. Examples of suitable Group VB metal oxides include vanadium oxides such as $VO$, $VO_2$, $V_2O_3$, $V_2O_5$, $V_3O_5$, $V_5O_9$, $V_6O_{13}$; niobium oxides such as $NbO$, $NbO_2$, $Nb_2O_5$; tantalum oxides such as $Ta_2O_5$; as well as hydrated oxides including vanadates such as $H_3VO_4$, niobic acid such as $Nb_2O_5.xH_2O$, $H_8Nb_6O_{19}.xH_2O$, and $[H_2Nb_6O_{16}]m$, tantalic acid; Group VB metal acid salts, such as $KVO_3$, $NaVO_3$, $Na_3VO_4$, $KNbO_3$, $NaNbO_3$, $KTaO_3$, and mixtures of Group VB metal oxides, hydrated metal oxides, and/or metal acid salts. Non-stoichiometric oxides are also suitable. Mixtures of Group VB metal oxides and/or Group VB metal phosphates can also be employed. The aforementioned examples are illustrative of the great variety of forms the catalyst can assume; however, the catalyst is not necessarily limited to only the recited examples. Other Group VB metal phosphates and oxides may be obtained which are equally suitable for the process of this invention. Preferably, the Group VB metal phosphate possesses a P/metal mole ratio no greater than about 3.0. Even more preferably, the Group VB metal phosphate possesses a P/metal mole ratio no greater than about 1.0. Most preferably, the Group VB metal phosphate possesses a P/metal mole ratio in the range from about 0.02 to about 1.0. Preferably, the Group VB metal is niobium and the catalyst is a niobium-containing compound. More preferably, the Group VB metal phosphate is $NbOPO_4$ and the hydrated forms of $NbOPO_4$. More preferably, the Group VB metal oxide is an oxide or hydrated oxide of niobium. Most preferably, the Group VB metal oxide is a hydrated niobium oxide.

Generally, the common Group VB metal oxides are commercially available; while the less common oxides can be prepared by methods known in the art, such as are described in *Comprehensive Inorganic Chemistry*, Vol. 3, J C. Bailar, Jr., H. J. Emeleus, R. Nyholm, A. F. Trotman-Dickenson, eds., Pergamon Press, Oxford, 1973, pp. 510–524 and 592–599.

The Group VB metal phosphate compounds are relatively easy to prepare. The preparations are described in *Comprehensive Inorganic Chemistry*, ibid., pp. 612–613. Preferably, the Group VB metal phosphate catalyst is prepared by reacting a catalyst precursor compound containing a Group VB metal with a phosphorus-containing compound, such as phosphoric acid, under conditions sufficient to generate the Group VB metal phosphate. Anhydrous or aqueous phosphoric acid can be employed, as can chlorinated or fluorinated phosphoric acids, or chlorinated or fluorinated phosphorus-containing compounds. Typical catalyst precursor compounds which can be employed as starting materials include the Group VB metal oxides, hydrated oxides, halides, alkoxides, and carboxylic acid salts. More specifically, the catalyst precursor is heated with phosphoric acid at about atmospheric pressure and at a temperature in the range from about 130° C. to about 200° C. The weight ratio of phosphoric acid to precursor compound is preferably in the range from about 5 to about 20, more preferably, in the range from about 7 to about 15, most preferably, about 10. The phosphoric acid is typically employed as an 85 weight percent aqueous solution; however, additional water can be used to obtain higher surface area materials. The length of time the precursor compound and phosphoric acid are heated varies depending on the quantity of metal compound employed and the amount of water which is to be driven off in the heating. Typically, however, the mixture is heated for about one to two hours; however longer times may be employed. After heating, the mixture which comprises a liquid phase and a solid phase is cooled. The liquid is decanted from the solid, and the solid is washed with water and filtered. The washing and filtering may be repeated several times to ensure the removal of excess acid and unwanted ions. The filtered solid is dried at a temperature in the range from about 80° C. to about 150° C. in air for a time in the range from about 2 hours to about 50 hours to yield the catalyst of the invention. Typically, the catalyst is heat treated or calcined prior to use. Preferably, the calcination is conducted at a temperature in the range from about 200° C. to about 500° C. for a time in the range from about 2 hours to about 50 hours.

Preferably, the Group VB metal phosphate or Group VB metal oxide compounds, described hereinbefore, are insoluble in the amination reaction mixture, thereby acting as heterogeneous catalysts. Optionally, any of the Group VB metal phosphate or Group VB metal oxide compounds can be synthesized and made insoluble by (a) depositing onto a support material, or (b) binding with a refractory metal oxide or a support precursor. Any support or binder material is acceptable provided that it it does not enhance the formation of undesirable cyclic products in the process of this invention. Suitable supports or binders include carbon and any refractory oxide such as alumina (hydrated and dehydrated forms), zirconia, boria, thoria, magnesia, titania, tantala, chromia, silica, kielselguhr, niobia, and mixtures of these materials. Suitable support precursors include hydrated metal oxides and metal alkoxides. Preferably, the support or binder material is alumina, silica, or titania. More preferably, the support or binder material is an alumina or a hydrated alumina, such as boehmite or pseudoboehmite alumina (aluminum oxyhydroxide). The support material typically has a surface area of at least about 0.1 m$^2$/g. Preferably, the support material has a surface area in the range from about 5 m$^2$/g to about 600 m$^2$/g, most preferably in the range from about 50 m$^2$/g to about 200 m$^2$/g. These surface areas are measured by the Brunauer-Emmett-Teller (BET) method. The BET method is described by R. B. Anderson, in *Experimental Methods in Catalytic Research*, pp 48–66, Academic Press, 1968.

The Group VB metal phosphate and Group VB metal oxide can be deposited onto the support material in any known fashion, such as by impregnation or by precipitation in situ from the catalyst preparation reaction. In these types of preparation the metal phosphate or oxide is adsorbed onto the support. Alternatively, the metal phosphate or oxide can be chemically reacted or bound onto the support. In this method a catalyst precursor compound is reacted with the hydroxyl functionalities of the support to yield a catalyst precursor chemically bound to the support. For example, niobium chloride reacts with the hydroxyl moieties of silica to yield niobium chloride bound through an oxygen to silicon. Typically, the niobium chloride or Group VB metal chloride is dissolved in a solvent to make a solution. Any solvent is acceptable provided that it is not reactive with the metal chloride or the supported metal chloride. Acceptable solvents include saturated hydrocarbons, such as pentane and hexane and aromatic hydrocarbons, such as benzene and toluene, as well as acetone, acetonitrile, chlorinated hydrocarbons and the like. Typically, the minimum amount of solvent is used to dissolve the metal chloride. The refractory oxide is added to the resulting solution in a metal chloride/refractory oxide weight ratio in the range from about 0.0005 to about 0.60. The mixture is then rotary evaporated to remove the solvent leaving a solid of a Group VB metal chloride supported on a refractory oxide. The solid is heated at a temperature in the range from about 50° C. to about 150° C. for a time in the range from about 1 hour to about 5 hours to yield a Group VB metal chloride bound to a refractory oxide.

The bound catalyst precursor can be converted into the Group VB oxide catalyst of the invention by hydrolysis or heating. Preferably, the supported oxide catalyst is niobium oxide on an alumina, silica, or titania support. More preferably, the supported oxide catalyst is niobium oxide on an alumina support prepared by dehydrating a mixture of hydrated niobium oxide and boehemite or pseudoboehmite alumina. Similarly, the bound catalyst precursor can be converted into the Group VB phosphate catalyst of the invention by reaction with phosphoric acid. For example, the Group VB metal chloride bound to a refractory oxide, described hereinbefore, can be heated with an excess of 85 weight percent phosphoric acid at a temperature in the range from about 130° C. to about 200° C. for a time in the range from about 1 hours to about 5 hours to yield a Group VB metal phosphate supported on a refractory oxide. Preferably, the supported phosphate catalyst is niobium phosphate on alumina, silica, or titania. More preferably, the supported phosphate catalyst is niobium phosphate on silica.

The amount of catalyst which is employed in the process of this invention is any amount which is effective in producing the desired alkyl-extended, alcohol-extended, or amine-extended piperazines or mixtures thereof. The amount of catalyst varies considerably depending upon the specific reactants and reaction conditions employed. Typically, in a batch reactor the amount of catalyst is in the range from about 0.1 weight percent to about 20 weight percent based on the weight of reactant amine. Preferably, the amount of catalyst is in the range from about 1 weight percent to about 15 weight percent based on the weight of reactant amine.

Generally, the process of this invention can be carried out in any suitable reactor, including batch reactors, continuous fixed-bed reactors, slurry reactors, fluidized bed reactors, and catalytic distillation reactors. Preferably, the reactor is a continuous fixed-bed reactor.

The reactants are contacted with the catalyst at any operable temperature which promotes the amination process of this invention and yields the desired alkyl-extended, alcohol-extended, or amine-extended piperazine products or mixtures thereof. Typically, the temperature is in the range from about 200° C. to about 350° C. Preferably, the temperature is in the range from about 240° C. to about 325° C. More preferably, the temperature is in the range from about 250° C. to about 315° C. Below the preferred lower temperature the conversion of aliphatic alcohol may be low. Above the preferred upper temperature the selectivity for alkyl-extended, alcohol-extended, and amine-extended piperazines may decrease.

Likewise, the reactants are contacted with the catalyst at any operable pressure which promotes the amination process of this invention and yields the desired alkyl-extended, alcohol-extended or amine-extended piperazine products or mixtures thereof. Typically, the pressure is sufficient to maintain the reactants in the liquid state at the temperature of the reaction. Preferably, the pressure is in the range from about atmospheric to about 4000 psig. More preferably, the pressure is in the range from about 100 psig to about 3000 psig. Most preferably, the pressure in the range from about 400 psig to about 2000 psig. In batch reactors the pressure is autogenous, and depends on the vapor pressures of the reactants and products and the temperature of the reaction.

When the process is conducted in a continuous flow reactor, the flow rate of the reactants can be varied. Generally, the aliphatic alcohol and the reactant amine are premixed to form a feed stream, which is fed into the reactor at any operable flow rate which yields the desired alkyl-extended, alcohol-extended, or amine-extended piperazine products. The flow rate is expressed as the liquid hourly space velocity (LHSV) and is given in units of grams of total reactants per milliliter of total reactor volume per hour, $g\ ml^{-1}\ hr^{-1}$. It is preferred to employ a liquid hourly space velocity of reactants in the range from about $0.1\ g\ ml^{-1}\ hr^{-1}$ to about $10.0\ g\ ml^{-1}\ hr^{-1}$; more preferably in the range from about $0.5\ g\ ml^{-1}\ hr^{-1}$ to about $4.0\ g\ ml^{-1}hr^{-1}$. It should be understood that the space velocity controls the residence time of the reactants in a continuous flow reactor.

When the process is conducted in a batch reactor, the reaction time determines the length of contact between the reactants and the catalyst. Any reaction time is acceptable which allows the amination reaction to proceed to the desired alkyl-extended, alcohol-extended, or amine-extended piperazine products The reaction time will depend on the quantity of reactants, the quantity of catalyst, the temperature of the reaction and desired degree of conversion. Preferably, the reaction time in a batch reactor is in the range from about 1 hour to about 20 hours.

When the aliphatic alcohol and the reactant amine are contacted in accordance with the process of this invention, the alcohol and the reactant amine react to form a mixture of alkyl-extended, alcohol-extended or amine-extended piperazine products, or mixtures thereof, and water is eliminated as a by-product. These products can be further described as linearly-extended materials. If the difunctional alcohol contains two or more hydroxyl moieties, the reactant amine may react at each hydroxyl. Thus, as noted hereinbefore, ethanol reacts with piperazine to yield N-ethylpiperazine or N,N'-diethylpiperazine, which are alkyl-extended piperazines. Likewise, ethylene glycol reacts with piperazine to yield predominantly N-(2-hydroxyethyl)piperazine, an alcohol-extended piperazine; and monoethanolamine reacts with piperazine to yield predominantly N-(2-aminoethyl)piperazine, an amine-extended piperazine. Higher amine-extended piperazine oligomers can also be produced, as in the reaction of piperazine with hydroxyethylpiperazine to yield 1,2-bis(piperazinyl)ethane and N,N'-bis(2-piperazinylethyl)piperazine. Other amine-extended piperazines which can be produced in the process of this invention include N,N'-bis(2-aminoethyl)piperazine, and N,N'-bis(2-aminoethyl)bispiperazine. Other alcohol-extended piperazines which can be produced in the process of this invention include N,N'-bis(2-hydroxyethyl)piperazine and N-(2-hydroxyethyl)bispiperazines. In addition to the linearly-extended products, it is possible to obtain certain undesirable cyclic by-products, including, for example, 1,4-diaza-[2.2.2]-bicyclooctane.

The preferred alcohol-extended and amine-extended piperazine products can be represented by the general formula:

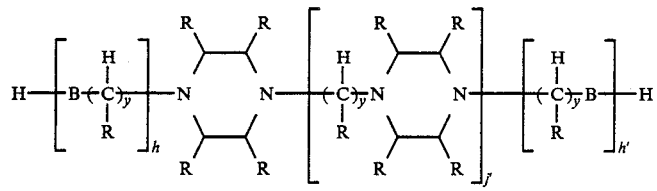

wherein each B is independently O or NR; each R is independently hydrogen, hydroxy, amino, an alkyl moiety of $C_1$–$C_{12}$ carbon atoms such as methyl, ethyl or propyl, a hydroxyalkyl or aminoalkyl moiety of $C_1$–$C_{12}$ carbon atoms, or a monocyclic aromatic moiety, such as phenyl, or tolyl; each y is independently an integer from 0 to about 12; h and h' are each independently integers from 0 to about 6; and j' is an integer from 0 to about 6. Some examples of products which satisfy this formula include N-(2-aminoethyl)piperazine, N-(2-hydroxyethyl)piperazine, bispiperazines and higher oligomers of piperazine. Preferably, each R is hydrogen. More preferably, each R is hydrogen, y is 1 or 2, j' is 1 or 2, h and h' are each independently 0–2, and each B is NR. Most preferably, each B is NR, each R is hydrogen, y is 2, h is 1, j' and h' are each 0, and the product is N-(2-aminoethyl)piperazine.

For the purposes of this invention, "conversion" is defined as the weight percentage of aliphatic alcohol lost as a result of reaction. The conversion can vary widely depending upon the reactants, the form of the catalyst, and the process conditions such as temperature, pressure, and flow rate. Within the preferred temperature range, as the temperature increases the conversion typically increases. Within the preferred space velocity range, as the space velocity increases the conversion typically decreases. Typically, the conversion of the aliphatic alcohol is at least about 10 weight percent. Preferably, the conversion is at least about 20 weight percent more preferably at least about 30 weight percent: even more preferably, 45 weight percent: and most preferably, at least about 65 weight percent.

Likewise, for the purposes of this invention "selectivity" is defined as the weight percentage of total products on a feed-free basis which forms a particular alkyl-extended, alcohol-extended, or amine-extended piperazine product. Typically, the selectivities also vary widely depending upon the reactants, the form of the catalyst, and the process conditions. Within the preferred temperature range, as the temperature increases the selectivity for alkyl-extended, alcohol-extended, and amine-extended piperazines typically decreases. Within the preferred space velocity range, as the space velocity increases, the selectivity for alkyl-extended, alcohol-extended, and amine-extended piperazines typically increases. Typically, the process of this invention achieves high selectivities to alkyl-extended, alcohol-extended or amine-extended piperazines or mixtures thereof. Preferably, the combined selectivity to alkyl-extended, alcohol-extended and/or amine-extended piperazines is at least about 40 weight percent, more preferably, at least about 60 weight percent, most preferably, at least about 80 weight percent. In the specific amination of monoethanolamine by piperazine, the product N-(2-aminoethyl) piperazine is produced in a selectivity of at least about 25 weight percent, more preferably, at least about 45 weight percent, most preferably, at least about 60 weight percent.

The following examples illustrate the invention, but are not intended to be limiting thereof. All percentages are given as weight percent, unless noted otherwise. In some instances the following abbreviations are used to indicate the reactants and products:

| | |
|---|---|
| MEA | monoethanolamine |
| EDA | ethylenediamine |
| AEEA | N-(2-aminoethyl)ethanolamine |
| DETA | diethylenetriamine |
| TETA | triethylenetetramine |
| PIP | piperazine |
| AEP | N-(2-aminoethyl)piperazine |
| DIAEP | N,N'-di(2-aminoethyl)piperazine |
| PEEDA | (piperazinylethyl)ethylenediamine |
| AEPEEDA | (N-aminoethylpiperazinylethyl)-ethylenediamine |
| PEDETA | (piperazinylethyl)diethylenetriamine |
| BISPIP | 1,2-bis(piperazinyl)ethane or bispiperazine |
| HEBIS | N-(2-hydroxyethyl)bispiperazine |
| TRISPIP | N,N'-bis(2-piperazinylethyl)-piperazine or trispiperazine |
| HETRIS | N-(2-hydroxyethyl)trispiperazine |
| DABCO | 1,4-diazabicyclo-[2.2.2]-octane |

EXAMPLE 1

(a) Preparation of Niobium Phosphate Catalyst

A mixture is prepared containing niobic acid, $Nb_2O_5 \cdot xH_2O$, (60.33 g 0.211 moles) and 85% phosphoric acid (602.20 g; 5.22 moles). The mixture is heated to 150° C. with stirring. The niobium oxide dissolves to form a pink solution, and upon further heating a precipitate forms. The precipitate is boiled in the phosphoric acid for about 2 hours. The mixture is cooled to room temperature, and the liquid is decanted from the precipitate. The precipitate is washed by adding 500 ml of water with stirring, after which the mixture is filtered. The washing and filtering cycle is repeated five times. The filtered solid is dried at 110° C. under air for 2½ days to yield a catalyst of niobium phosphate. The elemental analysis and X-ray diffraction spectrum of the catalyst are consistent with the composition $NbOPO_4$.

(b) Amination of Ethylene Glycol

Piperazine (51.6 g; 0.60 moles), ethylene glycol (12.4 g; 0.20 moles), and the catalyst of Example 1a (1.0 g) are loaded into a 300 ml, stirred autoclave. The reactor is sealed and flushed with nitrogen. The contents are heated for 4 hours at 300° C. Upon cooling to room temperature the products are analyzed by gas chromatography with the following results: conversion of EG, 98 percent; selectivities to HEP, 11.4 percent; BISPIP, 52.5 percent; DABCO, 5.2 percent; HEBIS, 6.2 percent; TRISPIP, 15 percent; HETRIS, 1.4 percent; and higher oligomers, 8.3 percent. It is seen that the amination products are predominantly linearly extended piperazines. Moreover, the quantity of undesirable internally cyclized products which is formed, such as DABCO, is low.

EXAMPLE 2

Amination of Hydroxyethylpiperazine

Piperazine, hydroxyethylpiperazine, solvent, and the catalyst of Example 1 are loaded into a 300 ml stirred autoclave in the proportions noted in Table I. The reactor is sealed and flushed with nitrogen, and the contents are heated as designated in Table I. Upon cooling to room temperature the product mixture is analyzed by gas chromatography with the results shown in Table I.

TABLE I

| Exp. 2 | PIP (g) | HEP (g) | PIP/HEP | Catalyst (g) | Solvent[1] (g) | T (°C.) | Time (hrs) |
|---|---|---|---|---|---|---|---|
| (a) | 30.0 | 15.0 | 3.0 | 2.0 | tol (25) | 300 | 15 |
| (b) | 10.0 | 15.0 | 1.0 | 1.0 | tol (25) | 300 | 5 |
| (c) | 20.0 | 20.0 | 1.5 | 0.7 | $H_2O$ (10) | 300 | 5 |
| (d) | 15.0 | 20.0 | 1.1 | 0.5 | $H_2O$/tol (12/20) | 285 | 3 |

| Exp. 2 | % HEP Conversion | % Selectivity (PIP-HEP free basis) | | | | | |
|---|---|---|---|---|---|---|---|
| | | DABCO | BISPIP | HEBIS | TRISPIP | HETRIS | Other[2] |
| (a) | 92 | 9.1 | 76.2 | 1.5 | 0 | 0 | 13.2 |
| (b) | 76 | 14.8 | 59.2 | 6.2 | 15.4 | 0 | 4.2 |
| (c) | 87 | 8.5 | 61.5 | 3.5 | 19.7 | 0 | 6.8 |
| (d) | 47 | 7.2 | 50.7 | 20.4 | 14.1 | 3.3 | 4.3 |

[1] tol = toluene
[2] Other includes cyclic TETA's, such as DIAEP and PEEDA, cyclic TEPA's, and unidentified compounds.

The data show that hydroxylethylpiperazine is aminated by piperazine in the presence of a catalyst of niobium phosphate to predominantly bispiperazine, which is an amine-extended piperazine. Moreover, the quantity of undesirable products, such as DABCO, is low.

EXAMPLE 3

Amination of Monoethanolamine

Three samples of the catalyst of Example 1 are calcined prior to use at the following temperatures: (a) 300° C., (b) 700° C., and (c) 1000° C. Each catalyst is employed in an amination reaction according to the following general procedure: Monoethanolamine (20.3 g; 0.33 moles), piperazine (28.7 g; 0.34 moles), and catalyst (1.0 g) are loaded into a 300 ml stirred batch reactor. The reactor is flushed with nitrogen three times, then heated to 300° C. The reaction mixture is maintained at 300° C. for five hours, then cooled to room temperature and analyzed by gas phase chromatography. A CAM (Carbowax amine deactivated) capillary column (30 m×0.25 mm dia.) is employed to measure total amine products. Isomer distributions are measured on an SE-30 capillary column (30 m×0.25 mm dia.). An SE-54 capillary column (30 m×0.25 mm dia.) is also used in analyzing for total amine content and isomer distribution. The results are presented in Table II.

TABLE II

| Ex. | % MEA Conversion | % Selectivity (PIP-MEA free basis) | | | | | | |
|---|---|---|---|---|---|---|---|---|
| | | EDA | DABCO | AEP | DI-AEP | PE-EDA | BIS-PIP | Higher |
| 13a | 78.6 | — | 0.49 | 74.7 | 8.8 | 10.1 | 3.1 | 2.9 |
| 13b | 50.5 | 4.5 | 0.62 | 72.8 | 7.6 | 11.5 | 3.1 | 7.3 |
| 13c | 25.7 | 15.6 | 5.6 | 64.7 | 3.1 | 8.2 | 2.8 | 2.4 |
| 24a | 12.7 | — | 1.1 | 92.6 | 1.1 | 4.0 | 1.1 | — |
| 24b | 41.8 | — | — | 71.9 | 7.2 | 13.4 | 1.3 | 6.3 |
| 24c | 50.7 | — | — | 70.1 | 8.0 | 13.3 | 1.9 | 6.6 |
| 24d | 76.0 | — | 1.1 | 56.1 | 11.2 | 10.7 | 4.1 | 16.8 |
| 35a | 75.5 | — | 1.2 | 60.1 | 11.1 | 12.1 | 3.2 | 12.2 |
| 35b | 58.6 | — | 1.2 | 64.9 | 9.3 | 12.4 | 2.8 | 9.2 |
| 6a | 75.0 | — | 1.3 | 61.9 | 10.1 | 12.5 | 3.1 | 11.1 |

[1]Catalyst of Example 3 is calcined at (a) 300° C., (b) 700° C., (c) 1000° C.
[2]Reaction of Example 4 is heated for (a) 5 min, (b) 2.5 hr, (c) 5.0 hrs, (d) 15 hrs.
[3]Catalyst of Example 5 is calcined at (a) 300° C. and (b) 500° C.

It is seen that monoethanolamine is aminated with piperazine in the presence of a niobium phosphate catalyst to predominantly aminoethylpiperazine. The conversion of monoethanolamine is greatest when the catalyst is calcined at 300° C. prior to use. In addition, the quantity of undesirable products, such as DABCO, is low.

EXAMPLE 4

(a) Preparation of Niobium Phosphate Catalyst

Silica (Shell Silica balls, 15.10 g) is dried at 300° C. overnight, then placed in a flask with niobium chloride, NbCl$_5$, (4.25 g, 15.7 mmoles). Acetonitrile is added to the flask with stirring in an amount sufficient to cover the balls and dissolve the niobium chloride. Thereafter, the acetonitrile is removed by rotary evaporation. Throughout the evaporation process the flask is rotated in order to coat the balls evenly with niobium chloride. The coated balls are heated at 50° C. for about 2 hours in vacuo, then cooled to room temperature to yield a composition of niobium chloride on silica. This composition is immediately added to 150 ml of 85 percent phosphoric acid at 160° C. The resulting mixture is heated to 195° C. and maintained there at for 5 minutes. The heated mixture is cooled to room temperature, whereupon 400 ml of water are added. The resulting aqueous mixture is stirred and filtered. The filtered solid is washed with water and refiltered. The washing and filtering procedures are repeated twice more. The washed solid is dried at 150° C. for 3 hours, and then calcined under air at 300° C. overnight to yield a catalyst of niobium phosphate bound to silica.

(b) Amination of Monoethanolamine

Monoethanolamine (20.5 g; 0.34 moles), piperazine (29.5 g; 0.34 moles), and the silica-supported niobium phosphate catalyst (1.0 g), prepared hereinabove, are loaded into a 300 ml stirred batch reactor. The reactor is flushed with nitrogen three times, then heated to 300° C. The reaction is maintained at 300° C. for the following times: (a) 5 minutes, (b) 2.5 hours, (c) 5 hours, (d) 15 hours, then cooled to room temperature and analyzed. The results are presented in Table II. It is seen that monoethanolamine is aminated with piperazine in the presence of a silica-supported niobium phosphate catalyst to predominantly aminoethylpiperazine; whereas, only low amounts of undesirable products, such as DABCO, are formed.

EXAMPLE 5

Amination of Monoethanolamine

Niobic acid, Nb$_2$O$_5$.xH$_2$O (Niobium Products Corp., CBMM number AD222) is pressed at a pressure of 20,000 psi into cylindrical pellets 1 inch in diameter by 1 inch in height. The pellets each contain approximately 25 g of niobic acid. The pressed pellets are dried at 120° C. for 4 hours, then slowly heated under air to a calcination temperature of (a) 300° C. or (b) 500° C. and held overnight. The calcined pellets are cooled, crushed, and sieved to 14–20 mesh size. The catalysts are employed in the amination of monoethanolamine by piperazine, as in Example 3, with the results shown in Table II. It is seen that monoethanolamine is aminated with piperazine in the presence of a catalyst of niobium oxide to predominantly aminoethylpiperazine and other amine-extended piperazines. The yield of undesirable products, such as DABCO, is low.

EXAMPLE 6

Amination of Monoethanolamine

Niobic acid, Nb$_2$O$_5$.xH$_2$O (Niobium Products Corp., CBMM number AD460) is pressed at 20,000 psig into cylindrical pellets 1 inch in diameter by 1 inch in height. The pressed pellets are dried at 120° C. for 4 hours, then heated slowly under air to a calcination temperature of 300° C. and held overnight. The calcined pellets are crushed and sieved to 14–20 mesh prior to use in the reactor. The catalyst is employed in Example 6(a) in the amination of monoethanolamine by piperazine, as in Example 3, with the results shown in Table II. The data show that monoethanolamine is aminated by piperazine in the presence of niobic acid to predominantly aminoethylpiperazine. The results are comparable to those of Example 5(a).

In Example 6(b) the niobic acid catalyst, prepared hereinabove, is loaded into a stainless steel, fixed-bed, continuous flow reactor (approximately 6 inches×½ inch diameter) fitted with glass wool plugs. A feedstream containing monoethanolamine and piperazine in a PIP/MEA mole ratio of 1.0 and additionally containing 18–20 weight percent water is fed through the catalyst bed at a variety of reaction temperatures, pressures, and flow rates. The liquid effluent from the reactor is collected and sampled by gas phase chromatography. The process conditions and results are presented in Table III.

$ml^{-1}$ $hr^{-1}$ the following results are obtained: conversion of MEA, 54.8 percent; selectivities to EDA, 0.60 percent; DABCO, 1.7 percent; AEEA, 0.89 percent; AEP, 57.0 percent; DIAEP, 5.7 percent; PEEDA, 10.4 percent; BISPIP, 7.4 percent; and other higher homo-

TABLE III [1]

| EX. 6(b) | Temp. (°C.) | P (psig) | LHSV g $ml^{-1}$ $hr^{-1}$ | % MEA Conv. | Selectivity [2] | | | | | | | | |
|---|---|---|---|---|---|---|---|---|---|---|---|---|---|
| | | | | | EDA | DABCO | DETA | AEEA | AEP | DIAEP | PEEDA | BISPIP | OTHER [3] |
| 1 | 280 | 1400 | 2 | 45.0 | 0.91 | 2.3 | — | 0.40 | 48.6 | 5.7 | 6.7 | 9.4 | 26.0 |
| 2 | 300 | 1400 | 2 | 84.6 | 0.80 | 5.0 | — | 0.67 | 26.2 | 4.4 | 3.1 | 14.6 | 45.3 |
| 3 | 285 | 1350 | 2 | 54.6 | 0.98 | 2.8 | — | 0.26 | 47.1 | 6.3 | 6.9 | 10.9 | 24.8 |
| 4 | 280 | 1200 | 1 | 48.6 | 0.61 | 2.4 | — | — | 51.9 | 6.2 | 8.6 | 9.9 | 20.4 |
| 5 | 280 | 1200 | 4 | 24.9 | 1.8 | 1.6 | — | 0.83 | 62.5 | 4.9 | 9.1 | 6.7 | 12.5 |
| 6 | 280 | 1200 | 4 | 25.3 | — | — | — | — | 71.9 | 5.1 | 7.4 | 8.2 | 7.5 |

[1] Feedstream comprises MEA and PIP in an MEA/PIP mole ratio of 1.0, and additionally contains 18-20 weight percent water.
[2] Calculated on feed-free and $H_2O$-free basis from GC area percentages corrected for individual response factors.
[3] Other products include branched TETA, linear and branched TEPA, higher piperazinyl homologues, and in (5) and (7) small amounts of ethylamine. No linear TETA is found in the product streams.

It is seen that monoethanolamine is aminated with piperazine in the presence of a niobium oxide catalyst to predominantly aminoethylpiperazine and higher amine-extended piperazines. Moreover, the yield of undesirable products, such as DABCO, is low.

EXAMPLE 7

(a) Preparation of Alumina-Supported Niobic Acid Catalyst

Boehmite or pseudoboehmite alumina (150.0 g; Davison Chemical Company: Alpha Alumina Monohydrate) and niobic acid (150.0 g; Niobium Products Corp., CBMM number AD460) are mixed together, and the mixture is pressed at 20,000 psig into cylindrical pellets 1 inch in diameter by 1 inch in height. Each pellet contains approximately 20 g of mixture. The pellets are dried at 120° C. for 5 hours, then heated slowly under air to a calcination temperature of 350° C. and held overnight. The calcined pellets are cooled, crushed, and sieved to 14-20 mesh to yield a boehmite-supported niobic acid catalyst.

(b) Amination of Monoethanolamine

The boehmite-supported niobic acid catalyst, prepared hereinabove, is employed in the continuous flow reactor of Example 6(b) with a feedstream of monoethanolamine and piperazine in a PIP/MEA mole ratio of 1.0 and additionally containing 18-20 weight percent water. At 285° C., 1400 psig, and a LHSV of about 1 g logues, 16.2 percent. It is seen that monoethanolamine is aminated with piperazine in the presence of a boehmite-supported niobic acid catalyst to predominantly aminoethylpiperazine, which is an amine-extended piperazine.

EXAMPLE 8

(a) Preparation of Alumina-Supported Niobic Acid Catalyst

Boehmite or pseudoboehmite alumina (20.0 g; Conoco Alumina Catapal SB; 100-325 mesh) and niobic acid (20.0 g; Niobium Products Corp., CBMM number AD460) are mixed together, and the mixture is pressed at 20,000 psig into cylindrical pellets 1 inch in diameter by 1 inch in height. Each pellet contains approximately 20 g of mixture. The pellets are dried at 120° C. for 5 hours, then heated slowly under air to a calcination temperature of 350° C. and held overnight. The calcined pellets are cooled, crushed, and sieved to 14-20 mesh prior to use to yield a boehmite-supported niobic acid catalyst.

(b) Amination of Monoethanolamine

The boehmite-supported niobic acid catalyst, prepared hereinabove, is loaded into the reactor of Example 6(b). A mixture comprising monoethanolamine, piperazine, ethylenediamine, diethylenetriamine, water, and optionally some DABCO, is fed through the reactor at a variety of process conditions with the results shown in Table IV.

TABLE IV

| EX. 8 | Feed (GC area % based on organics) [1] | | | | | MEA/PIP mole ratio | Temp. (°C.) | P (psig) | LHSV g $ml^{-1}$ $hr^{-1}$ |
|---|---|---|---|---|---|---|---|---|---|
| | EDA | MEA | PIP | DABCO | DETA | | | | |
| a | 7.24 | 30.31 | 53.76 | — | 7.68 | 1.3 | 300 | 1400 | 1.8 |
| b | 7.24 | 30.31 | 53.76 | — | 7.68 | 1.3 | 280 | 1380 | 0.76 |
| c | 7.24 | 30.31 | 53.76 | — | 7.68 | 1.3 | 280 | 1400 | 0.84 |
| d | 7.12 | 31.85 | 54.26 | — | 6.67 | 1.3 | 300 | 1400 | 0.92 |
| e | 6.20 | 29.68 | 55.39 | 2.47 | 6.21 | 1.2 | 300 | 1400 | 0.88 |
| f | 5.23 | 47.21 | 40.60 | 1.82 | 4.57 | 2.6 | 300 | 1400 | 0.88 |
| g | 5.23 | 47.21 | 40.60 | 1.82 | 4.57 | 2.6 | 282 | 1368 | 0.88 |

| EX. 8 | % MEA Conv. | Selectivity [2] | | | | | | |
|---|---|---|---|---|---|---|---|---|
| | | DABCO | AEEA | AEP | Linear TETA | DIAEP | PEEDA | BISPIP | OTHER [3] |
| a | 58.9 | 2.7 | 1.2 | 43.9 | — | 6.7 | 11.8 | 5.6 | 27.9 |
| b | 43.4 | 1.6 | 2.5 | 49.1 | 2.6 | 5.8 | 12.6 | 3.7 | 22.1 |
| c | 35.5 | 1.2 | 2.4 | 53.2 | 3.1 | 5.4 | 13.1 | 2.9 | 18.6 |
| d | 73.2 | 2.9 | — | 37.6 | — | 7.3 | 10.4 | 7.6 | 34.2 |
| e | 81.6 | 0.65 | — | 34.1 | — | 6.9 | 8.8 | 9.4 | 40.1 |
| f | 90.3 | — | 0.16 | 20.8 | — | 7.0 | 4.2 | 7.3 | 60.6 |

TABLE IV-continued

| g | 31.0 | — | 7.5 | 48.2 | — | 5.9 | 11.2 | 1.7 | 25.5 |

[1] Additionally, the feed contains 18–20 weight percent water.
[2] Calculated on feed-free and $H_2O$-free basis from GC area percentages corrected for individual response factors.
[3] Other products include branched TETA, linear and branched TEPA, higher piperazinyl homologues, and in (e) and (g) small amounts of ethylamine. No EDA or DETA is detected in the product mixtures.

It is seen that monoethanolamine is aminated with piperazine in the presence of a catalyst of boehmite-supported niobium oxide to predominantly aminoethylpiperazine and higher amine-extended piperazines.

EXAMPLE 9

(a) Preparation of Tantalum Phosphate Catalyst $TaCl_5$ (100.0 g, 0.28 moles) is added to 600 g of 85% phosphoric acid with stirring. The mixture is heated to 185° C., maintained there at for 1 hour, and then cooled overnight. After cooling, 500 ml of water are added to the mixture with stirring, and the mixture is filtered. The washing and filtering steps are repeated three times. The filtered solid is dried overnight at 120° C., then calcined at 300° C. under air over a second night to yield a tantalum phosphate catalyst.

(b) Amination of Monoethanolamine with Piperazine

Monoethanolamine (20.3 g; 0.33 moles), piperazine (28.7 g; 0.34 moles), and the tantalum phosphate catalyst (1.0 g), prepared hereinabove, are loaded into a 300 ml stirred batch reactor. The reactor is flushed with nitrogen three times, then heated to 300° C. The reaction mixture is maintained at 300° C. for five hours, then cooled to room temperature and analyzed with the following results: conversion of MEA, 11 percent; selectivities to AEP, 77.6 percent; DIAEP, 3.5 percent; PEEDA, 11.4 percent; BISPIP, 7.5 percent. There is no detectable DABCO or higher oligomers. The data show that monoethanolamine is aminated with piperazine in the presence of a tantalum phosphate catalyst to predominantly amine-extended piperazines.

EXAMPLE 10

(a) Preparation of Niobium Silico-phosphate Catalyst

A first mixture containing fumed silica (10.0 g; Cabosil M5) and 300.0 g of 85 % phosphoric acid is prepared and heated to 165° C. A second mixture containing niobic acid (60.26 g; Niobium Products Inc.) and 600.0 g of 85 % phosphoric acid is prepared and heated to 145° C. When all of the niobic acid has dissolved in the phosphoric acid, the first mixture is added to the second mixture. The combined mixtures are heated to 176° C. whereupon a precipitate forms. The precipitate and mother liquor are heated to 200° C., and then cooled to room temperature. The cooled mixture is diluted with 500 ml of water with stirring, and then filtered. The filtered precipitate is washed with 500 ml of water and filtered, three times each. The washed precipitate is dried overnight at 120° C. and then dried a secon night at 300° C. to yield a niobium silico-phosphate catalyst.

(b) Amination of Monoethanolamine with Piperazine

The amination of monoethanolamine with piperazine is conducted as in Example 3, except the catalyst is the niobium silico-phosphate, prepared hereinabove. The results are the following: conversion of MEA, 67.9 percent; selectivities to DABCO, 1.04 percent; AEP, 65.5 percent; DIAEP, 10.1 percent; PEEDA, 10.9 percent; BISPIP, 3.9 percent; and highers, 8.6 percent. The data show that monoethanolamine is aminated with piperazine in the presence of a niobium silico-phosphate catalyst to predominantly amine-extended piperazines.

EXAMPLE 11

(a) Preparation of Alumina-Supported Catalyst

Boehmite or pseudoboehmite alumina (60.0 g; Davison Alpha Alumina Monohydrate) and niobic acid (60.0 g; $Nb_2O_5.xH_2O$, Niobium Products Corp. CBMM number AD460) are mixed together. The mixture is pressed at 20,000 psi into cylindrical pellets 1 inch in diameter by 1 inch in height containing approximately 20 grams mixture per pellet. The pellets are dried at 120° C. for 5 hours, heated slowly to a calcination temperature of 400° C., and calcined at 400° C. overnight. The calcined pellets are cooled, crushed, and sieved to 14–20 mesh to yield a boehmite-supported niobic acid catalyst.

(b) Amination of Monoethanolamine

The boehmite-supported niobic acid catalyst, prepared hereinabove, is employed in the continuous flow reactor of Example 6(b) with a feedstream of monoethanolamine and N-aminoethylpiperazine in a MEA/AEP mole ratio of 1:1, and additionally containing about 18 weight percent water. The process conditions and results are presented in Table V.

TABLE V [1]

| EX. 11(b) | Temp. (°C.) | LHSV g ml$^{-1}$ hr$^{-1}$ | % MEA Conv. | DI-AEP | PE-EDA | AE-PEEDA | PE-DETA | PIP | DAB-CO | AEEA | BISPIP | OTHER [3] |
|---|---|---|---|---|---|---|---|---|---|---|---|---|
| | | | | | | Selectivity [2] | | | | | | |
| 1 | 280 | 0.84 | 35.5 | 34.9 | 13.2 | 7.4 | 1.9 | 7.8 | 5.2 | 2.5 | 1.6 | 25.6 |
| 2 | 285 | 0.88 | 35.9 | 35.5 | 13.6 | 7.5 | 1.9 | 5.2 | 4.4 | 4.0 | 1.0 | 26.9 |
| 3 | 295 | 1.62 | 41.3 | 29.8 | 11.2 | 6.8 | 1.9 | 8.4 | 5.1 | 2.0 | 1.8 | 32.5 |
| 4 | 295 | 0.83 | 67.7 | 21.8 | 7.0 | 6.1 | 1.3 | 7.8 | 5.8 | 0.4 | 3.7 | 45.7 |

[1] Feedstream comprises MEA and AEP in an MEA/AEP mole ratio of 1:1, and additionally contains about 18 weight percent water. The pressure in the reactor is maintained at 1395 psi.
[2] Calculated on feed-free and $H_2O$-free basis from GC area percentages corrected for individual response factors.
[3] Other products include branched EDA, DETA, branched and linear TETA's and TEPA's, and higher homologues of AEPEEDA, PEDETA, and BISPIP.

It is seen in Table V that boehmite-supported niobic acid catalyzes the amination of monoethanolamine by N-aminoethylpiperazine to amine-extended piperazines. Moreover, it is seen that the reaction produces DIAEP and PEEDA in a weight ratio DIAEP/PEEDA of nearly 3/1, and AEPEEDA and PEDETA in a weight ratio AEPEEDA/PEDETA of about 4/1.

What is claimed is:

1. A process for preparing alkyl-extended, alcohol-extended or amine-extended piperazines or mixtures thereof comprising contacting an aliphatic alcohol with a reactant amine, wherein at least one of the aliphatic alcohol or reactant amine contains a piperazine moiety, the contacting occurring in the presence of a catalyst under conditions such that an alkyl-extended, alcohol-extended or amine-extended piperazine or mixture thereof is formed, said catalyst being a composition containing a Group VB metal.

2. The process of claim 1 wherein the catalyst composition is a Group VB metal oxide or a Group VB metal phosphate or mixture thereof.

3. The process of claim 1 wherein the aliphatic alcohol is represented by the formula:

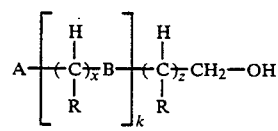

wherein A is H, OH or NHR; each B is independently NR or O; each R is independently hydrogen, hydroxyl, amino, an alkyl moiety of $C_1$-$C_{12}$ carbon atoms, a hydroxyalkyl or aminoalkyl moiety of $C_1$-$C_{12}$ carbon atoms, or a monocyclic aromatic moiety: x is an integer from 2 to about 12; k is an integer from 0 to about 150; and z is an integer from 0 to about 12.

4. The process of claim 3 wherein each R is hydrogen.

5. The process of claim 4 wherein x is 2 and z is 1.

6. The process of claim 5 wherein each R is hydrogen, A is $NH_2$, k is 0, z is 1, and the aliphatic alcohol is monoethanolamine.

7. The process of claim 1 wherein the aliphatic alcohol is represented by the formula:

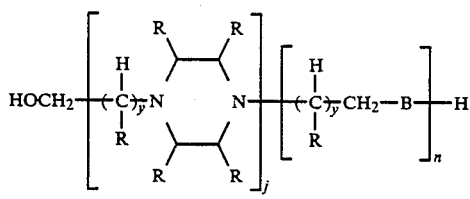

wherein each B is independently NR or O; each R is independently hydrogen, hydroxy, amino, an alkyl moiety of $C_1$-$C_{12}$ carbon atoms, a hydroxyalkyl or aminoalkyl moiety of $C_1$-$C_{12}$ carbon atoms, or a monocyclic aromatic moiety; each y is independently an integer from 0 to about 12; j is an integer from 1 to about 6; and n is an integer from 0 to about 6.

8. The process of claim 7 wherein each R is H, y is 1, j is 1 and n is 0, and the aliphatic alcohol is N-(2-hydroxyethyl)piperazine.

9. The process of claim 1 wherein the reactant amine is represented by the formula:

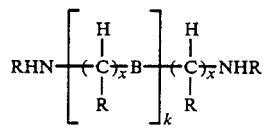

wherein each B is independently NR or O; each R is independently hydrogen, hydroxy, amino, an alkyl moiety of $C_1$-$C_{12}$ carbon atoms, a hydroxyalkyl or aminoalkyl moiety of $C_1$-$C_{12}$ carbon atoms, or a monocyclic aromatic moiety; each x is independently an integer from 2 to about 12; and k is an integer from 0 to about 150.

10. The process of claim 9 wherein the reactant amine is an ethylenepolyamine.

11. The process of claim 1 wherein the reactant amine is represented by the formula:

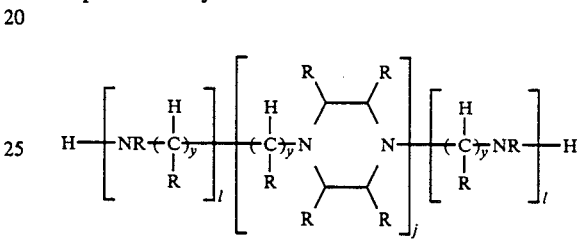

wherein each R is independently hydrogen, hydroxy, amino, an alkyl moiety of $C_1$-$C_{12}$ carbon atoms, a hydroxyalkyl or aminoalkyl moiety of $C_1$-$C_{12}$ carbon atoms, or a monocyclic aromatic moiety: each y is independently an integer from 0 to about 12; each l is independently an integer from 0 to about 6; and j is an integer from 1 to about 6.

12. The process of claim 11 wherein each R is hydrogen, y is 0, j is 1, each l is 0, and the compound is piperazine.

13. The process of claim 1 wherein the mole ratio of reactant amine to aliphatic alcohol is at least about 1.

14. The process of claim 2 wherein the Group VB metal is niobium.

15. The process of claim 14 wherein the catalyst is a niobium phosphate.

16. The process of claim 15 wherein the phosphorus to niobium metal mole ratio is no greater than about 1.0.

17. The process of claim 16 wherein the catalyst is $NbOPO_4$.

18. The process of claim 14 wherein the catalyst is an oxide or hydrated oxide of niobium.

19. The process of claim 18 wherein the catalyst is niobic acid supported on hydrated alumina.

20. The process of claim 1 wherein the amount of catalyst is in the range from about 0.1 weight percent to about 20 weight percent based on the weight of reactant amine.

21. The process of claim 1 wherein the temperature is in the range from about 200° C. to about 350° C.

22. The process of claim 1 wherein the pressure is in the range from about atmospheric to about 4000 psig.

23. The process of claim 1 wherein the liquid hourly space velocity is in the range from about 0.1 g ml$^{-1}$ hr$^{-1}$ to about 10.0 g ml$^{-1}$ hr$^{-1}$.

24. The process of claim 1 wherein the alcohol-extended and amine-extended piperazines are represented by the formula:

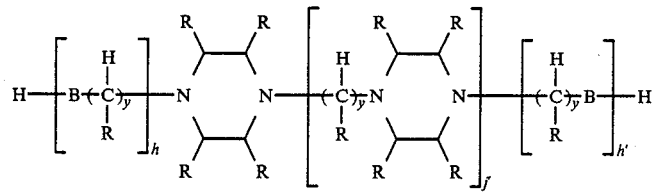

wherein each B is independently O or NR; each R is independently hydrogen, hydroxy, amino, an alkyl moiety of $C_1$–$C_{12}$ carbon atoms, a hydroxyalkyl or aminoalkyl moiety of $C_1$–$C_{12}$ carbon atoms, or a monocyclic aromatic moiety; each y is independently an integer from 0 to about 12; h and h' are independently integers from 0 to about 6; and j' is an integer from 0 to about 6.

25. The process of claim 24 wherein B is NR, R is hydrogen, y is 2, h is 1, j' and h' are 0, and the product is N-(2-aminoethyl)piperazine.

26. A process for preparing N-(2-aminoethyl)piperazine comprising contacting monoethanolamine with piperazine in the presence of a catalyst containing niobium oxide supported on boehmite alumina under conditions sufficient to prepare N-(2-aminoethyl)piperazine in a selectivity of at least about 20 weight percent 27. The process of claim 26 wherein the N-(2-aminoethyl)piperazine is produced in a selectivity of at least about 30 weight percent.

28. The process of claim 27 wherein the N-(2-aminoethyl)piperazine is produced in a selectivity of at least about 40 weight percent.

29. A process for preparing 1,2-bis(piperazinyle-thane) comprising contacting hydroxyethylpiperazine with piperazine in the presence of a catalyst containing niobium phosphate under conditions sufficient to prepare 1,2-bis(piperazinyl)ethane in a selectivity of at least about 40 weight percent.

* * * * *